United States Patent
Barbier et al.

[11] Patent Number: 5,827,883
[45] Date of Patent: Oct. 27, 1998

[54] DERMATOLOGICAL USE OF VITAMIN D DERIVATIVES

[75] Inventors: Pierre Barbier, Rixheim; Marc Muller, Huningue, both of France; Josef Stadlwieser, Basel, Switzerland

[73] Assignee: Hoffmann-La Roche Inc., Nutley, N.J.

[21] Appl. No.: 875,187

[22] PCT Filed: Jan. 17, 1996

[86] PCT No.: PCT/EP96/00176

§ 371 Date: Jul. 21, 1997

§ 102(e) Date: Jul. 21, 1997

[87] PCT Pub. No.: WO96/22776

PCT Pub. Date: Aug. 1, 1996

[30] Foreign Application Priority Data

Oct. 26, 1995 [EP] European Pat. Off. .............. 95101030

[51] Int. Cl.$^6$ .......................... A01N 37/02; A01N 37/08; C07C 69/74; C07C 69/66
[52] U.S. Cl. .......................... 514/546; 514/530; 514/550; 560/1; 560/121; 560/126; 560/128; 560/184; 560/188
[58] Field of Search ................................. 560/121, 1, 126, 560/184, 188, 128; 514/530, 550, 546

[56] References Cited

FOREIGN PATENT DOCUMENTS

| | | | |
|---|---|---|---|
| 63-183534 | 7/1988 | Japan | A61K 31/59 |
| 03275613 | 12/1991 | Japan | A61K 7/00 |
| WO 89/10353 | 11/1989 | WIPO . | |
| WO 9112807 A | 9/1991 | WIPO | A61K 31/59 |

OTHER PUBLICATIONS

K. Allewaert, et al. Bioorg. Med. Chem. Lett. vol. 3, No. 9 pp. 1859–1862 (1993).
M. Chodynski, et al. Steroids, vol. 56, No. 6, pp. 311–315 (1991).
K. Allewaert, et al. Steroids, vol. 59, No. 12 pp. 686–690 (1994).

*Primary Examiner*—Paul J. Killos
*Assistant Examiner*—Brian J. Davis
*Attorney, Agent, or Firm*—George W. Johnston; Patricia S. Rocha-Tramaloni; Robert A. Silverman

[57] ABSTRACT

A method of using vitamin D derivatives of the formula

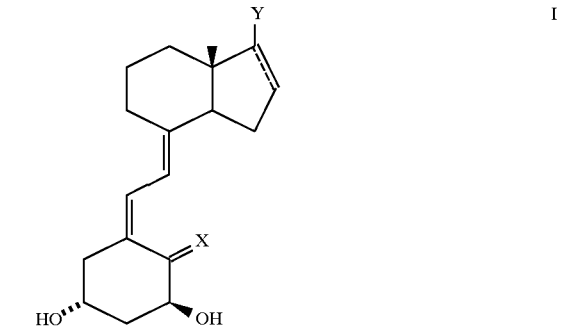

wherein
X is =CH$_2$ or H,H;
Y is a moiety —CH(CH$_3$)—(A)$_n$—C(O)—OR$^1$     (a)

—CH(CH$_3$)—CH$_2$—O—C(O)—R$^2$     (b)

or

—C(O)—OR$^1$     (c);

A is —CH=CH— or CH$_2$—CH$_2$—
R$^1$ is lower alkyl, cycloalkyl, cycloalkylmethyl, —CH$_2$R$^3$ or —CH$_2$—CH$_2$R$^3$;
R$^2$ is lower alkyl, cycloalkyl or R$^3$;
R$^3$ is hydroxy-lower alkyl, hydroxy-cycloalkyl or trifluoromethyl-hydroxy-lower-alkyl;
n is 0 or 1;
and the dotted bond in the five membered ring is optional; in the treatment of dermatological conditions, in particular keratinization disorders such as psoriasis, as well as acne and photodamaged skin, is described.

Vitamin D derivatives of the formula I above, wherein X, Y, A, R$^1$, R$^2$, R$^3$ and n are as set forth above; with the proviso that X is H,H when Y is —CH(CH$_3$)—CH$_2$—OC(O)—C(OH)(CH$_3$)$_2$ and the dotted bond in the five-membered ring is not present; as well as a process for the preparation of the compounds of formula I, and pharmaceutical compositions containing a compound of the formula I wherein X, Y, A, R$^1$, R$^2$, R$^3$ and n are set forth above; with the proviso that X is H,H when Y is —CH(CH$_3$)—CH$_2$—OC(O)—C(OH)(CH$_3$)$_2$ and the dotted bond in the five-membered ring is not present, are also described.

21 Claims, No Drawings

DERMATOLOGICAL USE OF VITAMIN D DERIVATIVES

The present invention relates to the use of vitamin D derivatives of the formula I

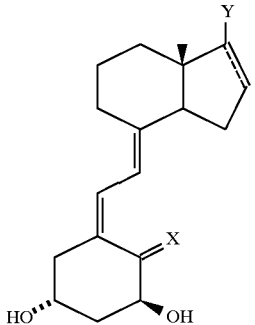

wherein
X is =CH$_2$ or H,H;
Y is a moiety

—CH(CH$_3$)—(A)$_n$—C(O)—OR$^1$ (a)

—CH(CH$_3$)—CH$_2$—O—C(O)—R$^2$ (b)

or

—C(O)—OR$^1$ (c);

A is —CH=CH— or CH$_2$—CH$_2$—
R$^1$ is lower alkyl, cycloalkyl, cycloalkylmethyl, —CH$_2$R$^3$ or —CH$_2$—CH$_2$R$^3$;
R$^2$ is lower alkyl, cycloalkyl or R$^3$;
R$^3$ is hydroxy-lower alkyl, hydroxy-cycloalkyl or trifluoromethyl-hydroxy-nieder-alkyl;
n is 0 or 1;
and the dotted bond in the five-membered ring is optional;
in the treatment of dermatological conditions, in particular keratinization disorders such as psoriasis, as well as acne and photodamaged skin; and to the use of the compounds of formula I in the manufacture of pharmaceutical compositions for the treatment of the aforementioned conditions.

The invention further relates to novel vitamin D derivatives of the formula I given above, wherein X, Y, A, R$^1$, R$^2$, R$^3$ and n have the above meaning; with the proviso that X is H,H when Y is a moiety

—CH(CH$_3$)—CH$_2$—OC(O)—C(OH)(CH$_3$)$_2$ and the dotted bond in the five-membered ring is absent; to a process for the preparation of the compounds of formula I, and to pharmaceutical compositions containing a compound of the formula I wherein X, Y, A, R$^1$, R$^2$, R$^3$ and n have the above meaning; with the proviso that X is H,H when Y is a moiety —CH(CH$_3$)—CH$_2$—OC(O)—C(OH) (CH$_3$)$_2$ and the dotted bond in the five-membered ring is absent.

The term "lower" as used herein denotes preferably moieties containing 1–5 carbon atoms, such as methyl, ethyl, isopropyl, isobutyl, tert.-butyl and 3-pentyl. Cycloalkyl moieties may be monocyclic such as cyclopropyl, cyclopentyl, cyclohexyl and cycloheptyl or bicyclic such as 6.6-dimetyl-bicyclo[3.3.1]hept-2-yl. Examples of hydroxy-lower alkyl moieties are 2-hydroxy-2-propyl, 2-hydroxy-2-methyl-butyl and 3-hydroxy-3-methyl-butyl. Examples of hydroxy-cycloalkyl are 1-hydroxy-cyclopentyl, 1-hydroxy-cyclohexyl and 1-hydroxy-cycloheptyl. A trifluoromethyl-hydroxy-lower alkyl moiety is, for example, 2-hydroxy-2-trifluoro-propyl.

In the structural formulas presented herein a broken bond (HO"") denotes that the substituent is below the plane of the paper and a wedged bond (—◀OH) denotes that the substituent is above the plane of the paper. In compounds of formula I wherein the dotted bond in the five-membered ring is absent, Y is above the plane of the paper (—◀Y). In the compounds of formula I wherein Y is a moiety (a) or (b) the carbon atom 20 (the one adjacent to the ring carbon atom) may have R or S configuration.

In accordance with this invention, the novel compounds of formula I can be prepared by a process which comprises removing the hydroxy protecting groups from a compound of the formula II

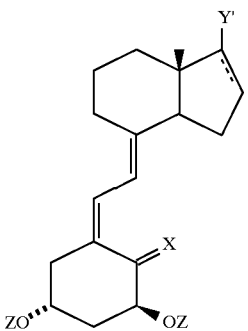

wherein Z is a protecting group and Y' is a moiety Y wherein any hydroxy groups contained therein are protected, with the proviso that the preparation of compounds wherein X is =CH$_2$ when Y is a moiety —CH(CH$_3$) —CH$_2$—OC(O)—C(OH)(CH$_3$)$_2$ and the dotted bond in the five-membered ring is absent is excluded, The protecting groups Z can be any conventional hydroxy protecting group. Examples of such groups are silyl ether protecting groups such as tert.-butyl-dimethylsilanyl. Another example of a hydroxy protecting group is tetrahydropyranyl. The removal of the hydroxy protecting groups Z can be effected in a manner known per se for the removal of such groups. For instance, silylether and tetrahydropyranyl groups can be removed by treatment with acidic reagents, such as hydrogen fluoride or tetrabutyl ammonium fluoride in tetrahydrofuran.

The compounds of formula II can be obtained by reacting a compound of the formula III

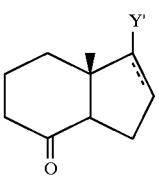

with a compound of the formula IV

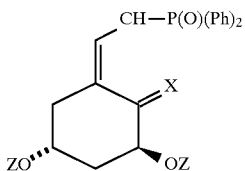

IV or by esterifying a compound of the formula V

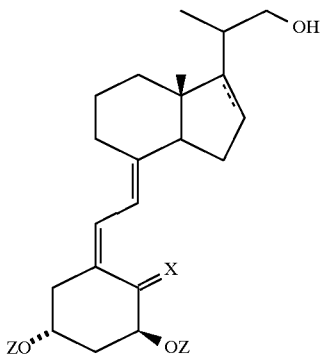

V with an acid of the formula R²COOH or a reactive derivative thereof, wherein in the above formulas Ph is phenyl; and Y', X and Z are as defined earlier.

The reaction of a compound of the formula III with a compound of the formula IV can be carried out under the conventional conditions of a Wittig reaction, i.e. in the presence of a base, e.g., butyl lithium, in an inert organic solvent, such as tetrahydrofuran. The esterification of a compound of formula V is suitably carried out by reacting the compound of formula V with the appropriate acid in the presence of a condensation agent such as dicyclohexylcarbodiimide or EDCI or under the conventional conditions of a Mitsunobu reaction. These reactions as well as the preparation of precursors of the compounds of formula II is described in detail in Examples A to S. With an appropriate selection of the starting materials the procedures set forth in Examples A to S can be applied also to the preparation of compounds of formula II and their precursors which are not explicitely described hereinafter.

EXAMPLE A

1-Ethinylcyclopentanol (25.0 g; 227 mmole) and 2,6-lutidine (29.2 g; 272 mmole) was dissolved in dry dichloromethane (250 ml); a solution of TES-triflate (56 ml; 249 mmole) in dry dichloromethane (50 ml) was added dropwise to the stirred reaction mixture at −78° C.; after complete addition stirring was continued for one hour. The reaction mixture was allowed to warm to 0° C.; 0.5M citric acid (250 ml) was added and stirring was continued for 30 min.; the organic layer was separated, washed with half sat. aqu. NaCl (100 ml) and dried over MgSO4; after filtration the solvent was removed in vacuo; the crude product was purified by distillation. 1-Ethinyl-1-triethylsilanyloxy-cyclopentane (A1) was obtained as colourless oil; bp.:52° C. (0.08 mbar).

Analogously, there was obtained
A2: 1-Ethinyl-1-triethylsilanyloxy-cyclohexane as a colourless oil from 1-Ethinyl-1-hydroxy-cyclohexane, bp (0.03 mbar): 78° C. (Kugelrohr);
A3: 1-Ethinyl-1-triethylsilanyloxy-cycloheptane as a colourless oil from 1-Ethinyl-1-hydroxy-cycloheptane, bp (0.03 mbar): 73° C. (Kugelrohr).

EXAMPLE B

Lindlar catalyst (250 mg) was prehydrogenated in hexane (40 ml) and pyridine (0.25 ml) for 30 min.; after addition of 1-Ethinyl-1-triethylsilanyloxy-cyclopentane (11.22 g; 50.0 mmole) dissolved in hexane (80 ml) hydrogenation was continued at ambient temperature and normal pressure until the uptake of hydrogen ceased; the catalyst was removed by filtration through a plug of neutral alumina (act. 3); after removal of the solvent under reduced pressure the crude product was purified by distillation. 1-Vinyl-1-triethylsilanyloxy-cyclopentane (B1) was obtained as a colourless oil; bp.: 100° C. (0.2 mbar), Kugelrohr.

Analogously, there was obtained
B2: 1-Vinyl-1-triethylsilanyloxy-cyclohexane as a colourless oil from 1-Ethinyl-1-triethylsilanyloxy-cyclohexane, bp (0.05 mbar): 100° C. (Kugelrohr);
B3: 1-Vinyl-1-triethylsilanyloxy-cycloheptane as a colourless oil from 1-Ethinyl-1-triethylsilanyloxy-cycloheptane, bp (0.07 mbar): 100° C. (Kugelrohr).

EXAMPLE C

1-Vinyl-1-triethylsilanyloxy-cyclopentane (9.06 g; 40.0 mmole) was ozonised at −78° C. in a mixture of dichloromethane (180 ml) and methanol (20 ml); dimethylsulfide (8.0 ml) was added and the reaction mixture was allowed to warm to ambient temperature. After extraction with half sat. aqu. NaCl (200 ml) the organic layer was dried over MgSO4; after filtration the solvent was removed in vacuo; the residual oil was diluted with tert.-BuOMe (200 ml) and DIBAL-H (1M solution in hexane; 44.0 ml; 44.0 mmole) was added dropwise under stirring at 0° C.; after one hour the reaction mixture was hydrolysed by dropwise addition of 2-propanol (8.0 ml), water (8.0 ml) and 0.5M citric acid (80 ml) at 0° C.; stirring was continued at ambient temperature for one hour. The organic layer was removed, washed with sat. aqu. NaCl (100 ml) and dried over MgSO4; after filtration the solvent was removed in vacuo; the crude product was purified by chromatography on silica gel (hexane : tert.-BuOMe—4:1) (1-Triethylsilanyloxy-cyclopentyl)-methanol (C1) was obtained as colourless oil.

Analogously, there was obtained
C2: (1-Triethylsilanyloxy-cyclohexyl)-methanol as a colourless oil from 1-Vinyl-1-triethylsilanyloxy-cyclohexane;
C3: (1-Triethylsilanyloxy-cycloheptyl)-methanol as a colourless oil from 1-Vinyl-1-triethylsilanyloxy-cycloheptane.

EXAMPLE D

1-Vinyl-1-triethylsilanyloxy-cyclopentane (9.06 g; 40.0 mmole) was dissolved in dry THF (100 ml); at 0° C. borane (1M in THF; 40.0 ml; 40.0 mmole) was added dropwise and the reaction mixture was stirred for one hour at ambient temperature. At 0° C. water (50 ml)was added dropwise, followed by NaBO3.4H2O (7.69 g; 50.0 mmole) and the mixture was stirred for additional 16 hours at ambient temperature; after filtration the organic layer was removed and concentrated in vacuo; the aqu. layer was extracted with tert.-BuOMe (2×50 ml); all organic layers were combined, washed with sat. aqu. NaCl (50 ml) and dried over MgSO4. After filtration the solvent was removed in vacuo, the crude product was chromatographed on silica gel (hexane:ethyl acetate—4:1). 2-(1-Triethylsilanyloxy-cyclopentyl)-ethanol (D1) was obtained as colourless oil.

Analogously there was obtained
D2: 2-(1-Triethylsilanyloxy-cyclohexyl)-ethanol as a colourless oil from 1-Vinyl-1-triethylsilanyloxy-cyclohexane;
D3: 2-(1-Triethylsilanyloxy-cycloheptyl)-ethanol as a colourless oil from 1-Vinyl-1-triethylsilanyloxy-cycloheptane.

EXAMPLE E 547 mg (1.76 mmol) of (1S,3aR,4S,7aR)-4-[(tert-Butyldimethyl-silanyloxy)7a-methyl-octahydro-inden-1-yl] ethanone in 5 ml of dry THF were added slowly at −78° C. to a solution of lithiumdiisopropylamin (1.94 mmol) in 5 ml of THF After 1 hour at this temperature the solution was quenched with an excess of trimethylsilylchloride (5.28 mmol) and evaporated to dryness. The residue was dissolved in 10 ml ethanol and ozonolysed until a persistent blue colour. Excess ozone was removed with argon and the resulting solution was added to a suspension of 669 mg (17.6 mmol) sodium borohydride in 10 ml ethanol at −30° C. After stirring for 1 hour at room temperature the reaction mixture was hydrolysed with water the ethanol was removed in vacuo and the residue extracted with ethyl acetate. The organic layer was washed with 0.5N aqueous citric acid solution, brine, dry over sodium sulfate and evaporated. Chromatography on silica gel (eluent n-hexane/ethyl acetate, 4:1) afforded 516 mg (39%) of pure (1S,3aR,4S,7aS)-4-(tert-butyl-dimethyl-silanyloxy)-7a-metghyl-octahydro-indene-1-carboxylic acid as a colourless solid.

EXAMPLE F 144 mg (0,218 mmol) of 2,2-Dimethyl-propionic acid-(5Z,7E)-(1S,3R,20S)-1,3-bis-(tert-butyl-dimethyl-silanyloxy)-20-methyl-9,10-seco-pregna-5,7,10 (19)-trien-21-yl ester was dissolved in dry toluene (3 ml) and cooled to −78° C. Dibal (0,55 ml of a 1,2M sol. in toluene; 0,65 mmol) was added dropwise. The reaction mixture was allowed to reach 0° C. and was then quenched with methanol (0,5 ml). A 2M aqueous potassium sodium tartrate solution (2 ml) was added and stirred till there was a clear phase separation. The organic phase was washed with brine and dried over $Na_2SO_4$. Removal of the solvent and column chromatography (eluent: n-hexane/ethyl-acetate 8/2) of the residue afforded 108 mg (86%) of (5Z,7E)-(1S,3R,20S)-1,3-bis-(tert-butyl-dimethyl-silanyloxy)-20-methyl-9,10-seco-pregna-5,7,10 (19)-trien-21-ol as a colourless foam.

EXAMPLE G 1.43 g (4.58 mmol) of (S)-1-[(1S,3aR,4S,7aR)-4-(tert-Butyldimethyl-silanyloxy)7a-methyl-octahydro-inden-1-yl] ethanol was dissolved in 15 ml pyridine and cooled to 0° C. 420 μl of $POCl_3$ were added slowly. The reaction mixture was stirred at room temperature overnight then poured into a buffer at pH 4, extracted with n-hexane. The organic solution was washed with brine, dried over sodium sulfate and evaporated to dryness. The residue was purified by column chromatography (eluent: n-hexane) to yield 516 mg (39%) of (E)-(3aR,4S,7aS)-4-(tert-Butyl-dimethyl-silanyloxy)-1-ethylidene-7a-methyl-octahydro-indene (E)-(3aR,4S,7aS)-4-(tert-Butyldimethyl-silanyloxy)-1-ethylidene-7a-methyl-octahydro-indene as a colourless oil.

EXAMPLE H 1740 mg of (S)-2-[(1R,3aR,4S,7aR)-4-(tert-butyl-dimethylsilanyloxy)-7a-methyl-octahydro-inden-1-yl]-propan-1-al was dissolved in anhydrous THF (35 ml). DBN (640 ml; 5,36 mmol) was added and the mixture was refluxed for four hours. The reaction mixture, after cooling, was poured in cold citric acid solution, extracted with ethyl-acetate, washed with brine and dried over $Na_2SO_4$. Removal of the solvent afforded a crude colourless oil (approximately 1:1 mixture at C(20)). The crude mixture was then dissolved in isopropanol (40 ml), cooled to 0° C., and $NaBH_4$ (232 mg; 6,13 mmol) was added. The cooling bath was removed and stirring was continued for half an hour at room temperature. The reaction mixture was poured in cold brine, extracted with ethyl-acetate, dried over $Na_2SO_4$. Removal of the solvent afforded a colourless oil. HPLC chromatography (eluent: n-hexane/ethyl-acetate 85:15) allowed the separation of both diastereoisomers affording 887 mg (50,7%) of the desired (R)-2-[(1R,3aR,4S,7aR)-4-(tert-Butyl-dimethyl-silanyloxy)-7a-methyl-octahydro-inden-1-yl]-propan-1-ol as a colourless oil.

EXAMPLE I 174 mg (0.59 mmol) of (E)-(3aR,4S,7aS)-4-(tert-Butyl-dimethyl-silanyloxy)-1-ethylidene-7a-methyl-octahydro-indene and 17.7 mg (0.59 mmol) of paraformaldehyde were dissolved in 2 ml of toluene at 0° C. and treated with 0.59 mmol of dimethylaluminiumchloride. The solution was stirred overnight at room temperature, then poured in buffer pH 4 and extracted with ethyl acetate. The organic phase was washed with brine, dried over sodium sulfate and evaporated to dryness. The residue was purified on silica gel (eluent hexane/ethylacetate, 4:1) to afford (R)-2-[(3aR,4S,7aS)-4-(tert-Butyl-dimethyl-silanyloxy)-7a-methyl-3a,4,5,6,7,7a-hexahydro-3H-inden-1-yl]-propan-1-ol as a colourless oil.

EXAMPLE J 198 mg (0,606 mmol) of (R)-2-[(1R,3aR,4S,7aR)-4-(tert-butyl-dimethyl-silanyloxy)-7a-methyl-octahydro-inden-1-yl]-propan-1-ol was dissolved in pyridine (3 ml) and cooled to 0° C. DMAP (18,5 mg; 0,152 mmol) was added followed by a slow addition of pivaloyl-chloride (97 ml; 0,79 mmol). The mixture was allowed to react for half an hour at 0° C. and half an hour at room temperature. The reaction mixture was poured in a cold aqueous HCl (25%) solution. Extraction with ether, washing with brine, drying over $Na_2SO_4$ and solvent removal gave a dark oil which was purified by column chromatography on silica gel (eluent: n-hexane/ethyl-acetate 97:3) affording 215 mg (86,3%) of 2,2-Dimethyl-propionic acid (R)-2-[(1R,3aR,4S,7aR)-4-(tert-butyl-dimethyl-silanyloxy)-7a-methyl-octahydro-inden-1-yl]-propyl ester (J1) as a yellow oil.

Analogously, there was obtained

J2: 2-Hydroxy-2-Methyl-propionic acid (R)-2-[(1R,3aR,4S,7aR)-4-(tert-butyl-dimethyl-silanyloxy)-7a-methyl-octahydro-inden-1-yl]-propyl ester as a yellow oil from (R)-2-[(1R,3aR,4S,7aR)-4-(tert-butyl-dimethyl-silanyloxy)-7a-methyl-octahydro-inden-1-yl]-propan-1-ol J3: 2-Hydroxy-2-methyl-propionic acid(S)-2-[(1R,3aR,4S,7aR)-4-(tert-butyl-dimethyl-silanyloxy)-7a-methyl-octahydro-inden-1-yl]-propyl ester as a yellow oil from (S)-2-[(1R,3aR,4S,7aR)-4-(tert-butyl-dimethyl-silanyloxy)-7a-methyl-octahydro-inden-1-yl]-propan-1-ol

EXAMPLE K 200 mg (0,612 mmol) of (S)-2-[(1R,3aR,4S,7aR)-4-(tert-butyl-dimethyl-silanyloxy)-7a-methyl-octahydro-inden-1-yl]-propan-1-ol was dissolved in THF (2 ml). $PPh_3$ (169 mg; 0,643 mmol) was added and the mixture cooled to 0° C. To this, a solution of DEAD (95 mg; 0,612 mmol) and 2-hydroxy-isobutyric acid (64 mg; 0,612 mmol) in THF (2 ml) was added dropwise via cannula. After four hours the reaction mixture was poured in cold water, extracted with ether and dried over $Na_2SO_4$. Removal of the solvent and silica gel column chromatography (eluent hexane/ethylacetate 85/15) of the residue afforded 232 mg (91%) of 2-hydroxy-2-methyl-propionic acid(S)-2-[(1R,3aR,4S,7aR)-4-(tert-butyl-dimethyl-silanyloxy)-7a-methyl-octahydro-inden-1-yl]-propyl ester (K1) as a yellow oil.

Analogously, there was obtained

K2: 2-Ethyl-2-hydroxy-butyric acid-(S)-2-[(1R,3aR,7aR)-4-(tert-butyl-dimethyl-silanyloxy)-7a-methyl-octahydro-inden-1-yl]ester as a yellow oil from (S)-2-[(1R,3aR,4S,7aR)-4-(tert-butyl-dimethyl-silanyloxy)-7a-methyl-octahydro-inden-1-yl]-propan-1-ol.

EXAMPLE L 2570 mg (E)-(R)-[(1R,3aR,4S,7aR)]-4-(tert-Butyl-dimethyl-silanyloxy)-7a-methyl-octahydro-inden-1-yl]pent-2-enoic acid ethyl ester was dissolved in absolute ethanol (50 ml). 245 mg of 10% palladium on carbon was added, the solution was degassed and maintained under an atmosphere of 1 atm of hydrogen overnight. The solution was filtered over a pad of silica gel and the solvent was removed. There were obtained 2188 mg (84,7%) of (R)-[(1R 3aR,4S,7aR) 1-4-(tert-Butyl-dimethyl-silanyloxy)-7a-methyl-indan-1-yl] pentanoic acid ethyl ester as a colourless oil pure enough to be used in the next step.

EXAMPLE M 490 mg of (R)-[(1R,3aR,4S,7aR)]-4-(tert-Butyl-dimethyl-silanyloxy)-7a-methyl-indan-1-yl]pentanoic acid ethyl ester was dissolved in a THF/ethanol mixture 1:1 (10 ml). A 4N NaOH aqueous solution (1 ml; 4 mmol) was added and stirred overnight. The reaction mixture was then poured in a cold citric acid solution. Extraction with ethyl acetate, drying over $Na_2SO_4$ and solvent removal gave a crude product which was purified by column chromatography (eluent: n-hexane/isopropanol 9:1) affording 450 mg (98,8%) of pure (R)-[(1R,3aR,4S,7aR)]-4-(tert-Butyl-dimethyl-silanoxy)-7a-methyl-indan-1-yl]pentanoic acid. 150 mg (0,41 mmol) of the previous acid was dissolved in dichloro-methane (5 ml); dicyclohexylcarbodiimide (DCC) (155 mg; 0,75 mmol); DMAP (11 mg; 0,08 mmol) and isopropanol (1 ml; 13 mmol) were added and stirring was continued overnight. The reaction mixture was poured in a cold 1N aqueous HCl solution. Extraction with ethyl acetate, washing with brine, drying over $Na_2SO_4$ and solvent removal gave a crude product which was purified by column chromatography on silica gel (eluant: n-hexane/ethyl-acetate 9:1) affording 167 mg (quantitative yield) of (R)-[(1R,3aR,4S,7aR)]-4-(tert-Butyl-dimethyl-silanyloxy)-7a-methyl-indan-1-yl]pentanoic acid isopropyl ester (M1) as a colourless oil.

Analogously, there was obtained

M2: (R)-4-[(1R,3aR,4S,7aR)-4-(tert-Butyl-dimethyl-silanyloxy)-7a-methyl-octahydro-inden-1-yl]-pentanoic acid 1-ethyl-propyl ester as a colourless oil from (R)-[(1R,3aR,4S,7aR)]-4-(tert-butyl-dimethyl-silanyloxy)-7a-methyl-indan-1-yl]pentanoic acid ethyl ester.

EXAMPLE N (S)-2-[(1R,3aR,7aR)-7a-Methyl-4-oxo-octahydro-inden-1-yl]-propionic acid (560.8 mg; 2.5 mmole) and dimethylaminopyridine (320.7 mg; 2.63 mmole) was dissolved in dry dichloromethane (25.0 ml); 4-toluene sulfonyl chloride (476.8 mg; 2.5 mmole) was added at 0° C. and the reaction mixture was stirred for 3 hours.

Dimethylaminopyridine (320.7 mg; 2.63 mmole) and hydroxymethylcyclopropane (216.3 mg; 3.0 mmole) was added; stirring was continued at 0° C. for 15 min; afterwards the reaction mixture was stored in a refrigerator for 16 hours.

The solvent was removed in vacuo; the residue was diluted with tert.-BuOMe (25.0 ml) and successively extracted with 1M citric acid (10.0 ml), water (10.0 ml) and sat. aqu. NaCl (10 ml); the organic layer was dried over $MgSO_4$. After filtration the solvent was removed in vacuo and the crude product was chromatographed on silica gel (hexane:ethyl acetate—85:15). (S)-2-[(1R,3aR,7aR)-7a-Methyl-4-oxo-octahydro-inden-1-yl]-propionic acid cyclopropylmethyl ester (N1)was obtained as a colourless oil.

Analogously, there was obtained

N2: (S)-2-[(1R,3aR,7aR)-7a-Methyl-4-oxo-octahydro-inden-1-yl]-propionic acid cyclopentylmethyl ester as a colourless oil from (S)-2-[(1R,3aR,7aR)-7a-Methyl-4-oxo-octahydro-inden-1-yl]-propionic acid and cyclopentyl methanol N3: (S)-2-[(1R,3aR,7aR)-7a-Methyl-4-oxo-octahydro-inden-1-yl]-propionic acid cyclohexylmethyl ester as a colourless oil from (S)-2-[(1R,3aR,7aR)-7a-Methyl-4-oxo-octahydro-inden-1-yl]-propionic acid and cyclohexyl methanol N4: (S)-2-[(1R,3aR,7aR)-7a-Methyl-4-oxo-octahydro-inden-1-yl]-propionic acid (1R,2S,5S)-6,6-dimethyl-bicyclo[3.1.1]hept-2-ylmethyl ester as a colourless oil from (S)-2-[(1R,3aR,7aR)-7a-Methyl-4-oxo-octahydro-inden-1-yl]-propionic acid and (−) trans myrtanol N5: (S)-2-[(1R,3aR,7aR)-7a-Methyl-4-oxo-octahydro-inden-1-yl]-propionic acid (1R,2R,5S)-6,6-dimethyl-bicyclo[3.1.1]hept-2-ylmethyl ester as a colourless oil from (S)-2-[(1R,3aR,7aR)-7a-Methyl-4-oxo-octahydro-inden-1-yl]-propionic acid and (−) cis myrtanol;

N6: (S)-2-[(1R,3aR,7aR)-7a-Methyl-4-oxo-octahydro-inden-1-yl]-propionic acid (1R,5S)-6,6-dimethyl-bicyclo [3.1.1]hept-2-en-2-ylmethyl ester as a colourless oil from (S)-2-[(1R,3aR,7aR)-7a-Methyl-4-oxo-octahydro-inden-1-yl]-propionic acid and (−) myrtenol;

N7: (S)-2-[(1R,3aR,7aR)-7a-Methyl-4-oxo-octahydro-inden-1-yl)]-propionic acid 1-tiethylsilanyloxy-cyclopentylmethyl ester as a colourless oil from (S)-2-[(1R,3aR,7aR)-7a-Methyl-4-oxo-octahydro-inden-1-yl]-propionic acid and (1-Triethylsilanyloxy-cyclopentyl)-methanol;

N8: (S)-2-[(1R,3aR,7aR)-7a-Methyl-4-oxo-octahydro-inden-1-yl]-propionic acid 1-triethylsilanyloxy-cyclohexylmethyl ester as a colourless oil from (S)-2-[(1R,3aR,7aR)-7a-Methyl-4-oxo-octahydro-inden-1-yl]-propionic acid and (1-Triethylsilanyloxy-cyclohexyl)-methanol;

N9: (S)-2-[(1R,3aR,7aR)-7a-Methyl-4-oxo-octahydro-inden-1-yl]-propionic acid 1-triethylsilanyloxy-cycloheptylmethyl ester as a colourless oil from (S)-2-[(1R,3aR,7aR)-7a-Methyl-4-oxo-octahydro-inden-1-yl]-propionic acid and (1-Triethylsilanyloxy-cycloheptyl)-methanol;

N10: (S)-2-[(1R,3aR,7aR)-7a-Methyl-4-oxo-octahydro-inden-1-yl)]-propionic acid 2-(1-tiethylsilanyloxy-cyclopentyl)-ethyl ester as a colourless oil from (S)-2-[(1R,3aR,7aR)-7a-Methyl-4-oxo-octahydro-inden-1-yl]-propionic acid and 2-(1-Triethylsilanyloxy-cyclopentyl)-ethanol;

N11: (S)-2-[(1R,3aR,7aR)-7a-Methyl-4-oxo-octahydro-inden-1-yl]-propionic acid 2-(1-triethylsilanyloxy-cyclohexyl)-ethyl ester as a colourless oil from (S)-2-[(1R,3aR,7aR)-7a-Methyl-4-oxo-octahydro-inden-1-yl]-propionic acid and 2-(1-Triethylsilanyloxy-cyclohexyl)-ethanol;

N12: (S)-2-[(1R,3aR,7aR)-7a-Methyl-4-oxo-octahydro-inden-1-yl]-propionic acid 2-(1-triethylsilanyloxy-cycloheptyl)-ethyl ester as a colourless oil from (S)-2-[(1R,3aR,7aR)-7a-Methyl-4-oxo-octahydro-inden-1-yl]-propionic acid and 2-(1-Triethylsilanyloxy-cycloheptyl)-ethanol.

EXAMPLE O 207 mg of 2,2-Dimethyl-propionic acid (R)-2-[(1R,3aR,4S,7aR)-4-(tert-butyl-dimethyl-silanyloxy)-7a-methyl-octahydro-inden-1-yl]-propyl ester was dissolved in THF (2.5 ml) and concentrated aqueous HF (40%) was added dropwise at room temperature and stirred overnight. The mixture was poured in a cold saturated bicarbonate solution, extracted with ethyl acetate and dried over $Na_2SO_4$. Removal of the solvent afforded the corresponding alcohol. The alcohol was dissolved in DMF (5 ml) and PDC (285 mg; 0,756 mmol) was added portion-wise over a period of ten minutes. The reaction was finished after one hour at room temperature. The mixture was poured in cold brine, extracted with a 1:1 mixture of ethyl acetate/hexane and dried over $Na_2SO_4$. Removal of the solvent and column chromatography (eluent n-hexane/ethyl-acetate 82:18) afforded 133 mg (89,6%) of 2,2-Dimethyl-propionic acid (R)-2-[(1R,3aR,7aR)-7a-methyl-4-oxo-octahydro-inden-1-yl]propyl ester as a yellow oil.

In analogy there was obtained

R2: (R)-4-[(1R,3aR,7aR)-7a-Methyl-4-oxo-octahydro-inden-1-yl]-pentanoic acid isopropyl ester as a colourless oil from (R)-4-[(1R,3aR,4S,7aR)-4-(tert-Butyl-dimethyl-silanyloxy)-7a-methyl-octahydro-inden-1-yl]pentanoic acid isopropyl ester;

R3: (R)-4-[(1R,3aR,7aR)-7a-Methyl-4-oxo-octahydro-inden-1-yl]pentanoic acid 1-ethyl-propyl ester as a colourless oil from (R)-4-[(1R,3aR,4S,7aR)-4-(tert-Butyl-dimethyl-silanyloxy)-7a-methyl-octahydro-inden-1-yl]-pentanoic acid 1-ethyl-propyl ester;

R4: 2,2-Dimethyl-propionic acid (R)-2-[(3aR,7aS)-7a-methyl-4-oxo-3a,4,5,6,7,7a-hexahydro-3H-inden-1-yl]-propyl ester from 2,2-Dimethyl-propionic acid (R)-2-[(3aR,4S,7aS)-4-(tert-butyl-dimethyl-silanyloxy)-7a-methyl-3a,4,5,6,7,7a-hexahydro-3H-inden-1-yl]-propyl ester;

R5: (E)-(R)-4-[(1R,3aR,7aR)-7a-methyl-4-oxo-octahydro-inden-1-yl]pent-2-enoic acid ethyl ester as a yellow oil from (E)-(R)-4-[(1R,3aR,4S,7aR)-4-(tert-butyl-dimethyl-silanyloxy)-7a-methyl-octahydro-inden-1-yl]-pent-2-enoic acid ethyl ester;

R6: (R)-4-[(1R,3aR,7aR)-7a-Methyl-4-oxo-inden-1-yl]-pentanoic acid ethyl ester as a colourless oil from (R)-[(1R,3aR,4S,7aR)]-4-(tert-butyl-dimethyl-silanyloxy)-7a-methyl-inden-1-yl]pentanoic acid ethyl ester.

EXAMPLE P 107 mg of the keto-alcohol 2-methyl-2-hydroxy-propionic acid-(R)-2-[(1R,3aR,7aR)-7a-methyl-4-oxo-octahydro-inden-1-yl]propyl-ester was dissolved in THF (4 ml) and cooled to 0° C. Then were added sequentially trimethylsilylimidazol (52,9 ml; 0,361 mmol), imidazole (12,3 mg; 0,18 mmol), trimethylchlorosilane (22,8 ml; 0,18 mmol) and the mixture stirred for half an hour.

The reaction mixture was poured in cold brine, extracted with ether and dried over $Na_2SO_4$. Removal of the solvent and column chromatography (eluent: n-hexane/ethyl-acetate 95/5) of the residue afforded 123 mg of 2-methyl-2-trimethyl-silanyloxy-propionic acid-(R)-2-[(1R,3aR,7aR)-7a-methyl-4-methyl-4-oxo-octahydro-inden-1-yl]-propyl ester (P1)as a colourless oil.

Analogously, there was obtained

P2: 2-Methyl-2-trimethylsilanyloxy-propionic acid(S)-2-[(1R,3aR,7aR)-7a-methyl-4-oxo-octahydro-inden-1-yl]-propyl ester as a colourless oil from 2-Hydroxy-2-methyl-propionic acid(S)-2-[(1R,3aR,4S,7aR)-4-(tert-butyl-dimethyl-silanyloxy)-7a-methyl-octahydro-inden-1-yl]-propyl ester;

P3: 2-Ethyl-2-trimethylsilanyloxy-butyric acid-(S)-2-[(1R,3aR,7aR)-7a-methyl-4-oxo-octahydro-inden-1-yl]propyl ester as a colourless oil from 2-Ethyl-2-hydroxy-butyric acid-(S)-2-[(1R,3aR,7aR)-4-(tert-butyl-dimethyl-silanyloxy)-7a-methyl-octahydro-inden-1-yl]propyl ester;

P4: (1S,3aR,7aS)-7a-Methyl-4-oxo-octahydroindene-1-carboxylic acid 3-methyl-3-trimethylsilanyloxy-butyl ester from (1S,3aR,4S,7aS)-4-(tert-Butyl-dimethyl-silanyloxy)-7a-methyl-octahydro-indene-1-carboxylic acid 3-hydroxy-3-methyl-butyl ester
MS (EI): $m/e$=339 (M$^{\cdot+}$—CH3)

EXAMPLE Q

In accordance with the oxidation step described in Example P there was obtained 2,2-Dimethyl-propionic acid (S)-2-[(1R,3aR,7aR)-7a-methyl-4-oxo-octahydro-inden-1-yl]propyl ester as a yellow oil from 2,2-Dimethyl-propionic acid (S)-2-[(1R,3aR,4S,7aR)-4-hydroxy-7a-methyl-octahydro-inden-1]-yl-propyl ester.

EXAMPLE R 62 mg (0,108 mmol) of (5Z,7E)-(1S,3R,20S)-1,3-bis-(tert-butyl-dimethyl-silanyloxy)-20-methyl-9,10-seco-pregna-5,7,10 (19)-trien-21-ol was dissolved in dichloromethane (3 ml). Then DCC (33,4 mg; 0,162 mmol), DMAP (2,6 mg; 0,022 mmol) and isovaleric acid (23,8 mg; 0,216 mmol) were added and the mixture was stirred overnight. The solvent was removed and the residue was purified by column chromatography (eluent: n-hexane/ethyl-acetate 97/3) affording 65 mg (91%) of 3-methyl-butyric acid (5Z,7E)-2-[(1S,3R,20S)-1,3-bis-(tert-butyl-dimethyl-silanyloxy)-20-methyl-9,10-seco-pregna-5,7,10 (19)-trien-21-yl]-propyl ester (R1) as a colourless oil.

Analogously, there was obtained

R2: 1:1 Mixture of (R)-and-(S)-3-Hydroxy-3-trifluoromethyl-butyric acid-(5Z,7E)-(1S,3R,20S)-1,3-bis-(tert-butyl-dimethyl-silanyloxy)-20-methyl-9,10-seco-pregna-5,7,10 (19)-trien-21-yl ester as a colourless oil from alpha-(2-amino-5-chlorophenyl)-2-furanmethanimine R3: 1:1 Mixture of (R)-and-(S)-3-hydroxy-3-methyl-pentanoic acid-(5Z,7E)-(1S,3R,20S)-1,3-bis-(tert-butyl-dimethyl-silanyloxy)-20-methyl-9,10-seco-pregna-5,7,10 (19)-trien-21-yl ester as a colourless oil from alpha-(2-amino-5-chlorophenyl)-2-furanmethanimine R4: 2-Hydroxy-2-methyl-propionic acid (7E)-(1R,3R,20R)-1,3-bis-(tert-butyl-dimethyl-silanyloxy)-20-methyl-19-nor-9,10-seco-pregna-5,7,16-triene-21-yl ester from (7E)-(1R,3R,20R)-1,3-bis-(tert-butyl-dimethyl-silanyloxy)-20-methyl-19-nor-9,10-seco-pregna-5,7,16-triene-21-ol

EXAMPLE S

[3S-(3alpha,5beta,Z)]-2-[2-[3,5-bis-[[(1,1-dimethylethyl) dimethylsilyl]oxy]cyclohexylidene]ethyl]diphenyl phosphine oxide; (456.7 mg; 0.8 mmole) was dissolved in dry THF (5.0 ml), n-BuLi (~1.6M solution in hexane: 0.5 ml)

was added at −78° C. and the mixture was stirred for 30 min.; a solution of (S)-2-[(1R,3aR,7aR)-7a-Methyl-4-oxo-octahydro-inden-1-yl]-propionic acid cyclopropylmethyl ester (111.4 mg; 0.4 mmole) in dry THF (1.0 ml) was added and stirring was continued at −78° C. for an additional two hours. The reaction mixture was allowed to warm to ambient temperature, 0.1M citric acid (10.0 ml) and sat. aqu. NaCl (5.0 ml) were added; stirring was continued for 15 min. The organic layer was separated and concentrated in vacuo; the aqu. layer was extracted with t-BuOMe (3×5 ml); all organic layers were combined, washed with sat. aqu. NaCl (5.0 ml) and dried over MgSO4. After filtration the solvent was removed in vacuo and the crude product was chromatographed on silica gel (hexane:t-BuOMe—90:10) (7E)-(1R,3R,20S)-1,3-Bis-(tert-butyl-dimethyl-silanyloxy)-20-methyl-19-nor-9,10-seco-pregna-5,7-dien-21-oic acid cyclopropylmethyl ester (S1) was obtained as a colourless oil.

Analogously, there was obtained

S2: (7E)-(1R,3R,20S)-1,3-Bis-(tert-butyl-dimethyl-silanyloxy)-20-methyl-19-nor-9,10-seco-pregna-5,7-dien-21-oic acid cyclopentylmethyl ester as a colourless oil from (S)-2-[(1R,3aR,7aR)-7a-Methyl-4-oxo-octahydro-inden-1-yl]-propionic acid cyclopentylmethyl ester and [3S-(3alpha,5beta,Z)-2-[2-[3,5-bis-[[(1,1-dimethylethyl)dimethylsilyl]oxy]cyclohexylidene]ethyl] diphenyl phosphine oxide;

S3: (7E)-(1R,3R,20S)-1,3-Bis-(tert-butyl-dimethyl-silanyloxy)-20-methyl-19-nor-9,10-seco-pregna-5,7-dien-21-oic acid cyclohexylmethyl ester as a colourless oil from (S)-2-[(1R,3aR,7aR)-7a-Methyl-4-oxo-octahydro-inden-1-yl]-propionic acid cyclohexylmethyl ester and [3S-(3alpha,5beta,Z)]-2-[2-[3,5-bis-[[(1,1-dimethylethyl)dimethylsilyl]oxy]cyclohexylidene]ethyl] diphenyl phosphine oxide;

S4: (7E)-(1R,3R,20S)-1,3-Bis-(tert-butyl-dimethyl-silanyloxy)-20-methyl-19-nor-9,10-seco-pregna-5,7-dien-21-oic acid (1S,2S,5S)-6,6-dimethyl-bicyclo[3.1.1]hept-2-ylmethyl ester as a colourless oil from (S)-2-[(1R,3aR,7aR)-7a-Methyl-4-oxo-octahydro-inden-1-yl]-propionic acid (1R,2S,5S)-6,6-dimethyl-bicyclo[3.1.1]hept-2-ylmethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S5: (7E)-(1R,3R,20S)-1,3-Bis-(tert-butyl-dimethyl-silanyloxy)-20-methyl-19-nor-9,10-seco-pregna-5,7-dien-21-oic acid (1S,2R,5S)-6,6-dimethyl-bicyclo[3.1.1]hept-2-ylmethyl ester as a colourless oil from (S)-2-[(1R,3aR,7aR)-7a-Methyl-4-oxo-octahydro-inden-1-yl]-propionic acid (1R,2R,5S)-6,6-dimethyl-bicyclo[3.1.1]hept-2-ylmethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S6: (7E)-(1R,3R,20S)-1,3-Bis-(tert-butyl-dimethyl-silanyloxy)-20-methyl-19-nor-9,10-seco-pregna-5,7-dien-21-oic acid (1R,5S)-6,6-dimethyl-bicyclo[3.1.1]hept-2-en-2-ylmethyl ester as a colourless oil from (S)-2-[(1R,3aR,7aR)-7a-Methyl-4-oxo-octahydro-inden-1-yl]-propionic acid (1R,5S)-6,6-dimethyl-bicyclo[3.1.1]hept-2-en-2-ylmethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S7: (7E)-(1R,3R,20S)-1,3-Bis-(tert-butyl-dimethyl-silanyloxy)-20-methyl-19-nor-9,10-seco-pregna-5,7-dien-21-oic acid 1-triethylsilanyloxy-cyclopentylmethyl ester as a colourless oil from (S)-2-[(1R,3aR,7aR)-7a-methyl-4-oxo-octahydro-inden-1-yl)]-propionic acid 1-tiethylsilanyloxy-cyclopentylmethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S8: (7E)-(1R,3R,20S)-1,3-Bis-(tert-butyl-dimethyl-silanyloxy)-20-methyl-19-nor-9,10-seco-pregna-5,7-dien-21-oic acid 1-triethylsilanyloxy-cyclohexylmethyl ester as a colourless oil from (S)-2-[(1R,3aR,7aR)-7a-methyl-4-oxo-octahydro-inden-1-yl]-propionic acid 1-triethylsilanyloxy-cyclohexylmethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S9: (5Z,7E)-(1R,3R,20S)-1,3-Bis-(tert-butyl-dimethyl-silanyloxy)-20-methyl-9,10-seco-pregna-5,7,10-trien-21-oic acid 1-triethylsilanyloxy-cyclohexylmethyl ester as a colourless oil from (S)-2-[(1R,3aR,7aR)-7a-methyl-4-oxo-octahydro-inden-1-yl]-propionic acid 1-triethylsilanyloxy-cyclohexylmethyl ester and [3S-(3alpha,5beta,Z)]-2-[2-[2-methylene-3,5-bis-[[(1,1-dimethylethyl)dimethylsilyl]oxy]cyclohexylidene]ethyl] diphenyl phosphine oxide;

S10: (7E)-(1R,3R,20S)-1,3-Bis-(tert-butyl-dimethyl-silanyloxy)-20-methyl-19-nor-9,10-seco-pregna-5,7-dien-21-oic acid 1-triethylsilanyloxy-cycloheptylmethyl ester as a colourless oil from (S)-2-[(1R,3aR,7aR)-7a-methyl-4-oxo-octahydro-inden-1-yl]-propionic acid 1-triethylsilanyloxy-cycloheptylmethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S11: (7E)-(1R,3R,20S)-1,3-Bis-(tert-butyl-dimethyl-silanyloxy)-20-methyl-19-nor-9,10-seco-pregna-5,7-dien-21-oic acid 2-(1-triethylsilanyloxy-cyclopentyl)-ethyl ester as a colourless oil from (S)-2-[(1R,3aR,7aR)-7a-methyl-4-oxo-octahydro-inden-1-yl)]-propionic acid 2-(1-tiethylsilanyloxy-cyclopentyl)-ethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S12: (7E)-(1R,3R,20S)-1,3-Bis-(tert-butyl-dimethyl-silanyloxy)-20-methyl-19-nor-9,10-seco-pregna-5,7-dien-21-oic acid 2-(1-triethylsilanyloxy-cyclohexyl)ethyl ester as a colourless oil from (S)-2-[(1R,3aR,7aR)-7a-methyl-4-oxo-octahydro-inden-1-yl]-propionic acid 2-(1-triethylsilanyloxy-cyclohexyl)-ethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S13: (7E)-(1R,3R,20S)-1,3-Bis-(tert-butyl-dimethyl-silanyloxy)-20-methyl-19-nor-9,10-seco-pregna-5,7-dien-21-oic acid 2-(1-triethylsilanyloxy-cycloheptyl) ethyl ester as a colourless oil from (S)-2-[(1R,3aR,7aR)-7a-methyl-4-oxo-octahydro-inden-1-yl]-propionic acid 2-(1-triethylsilanyloxy-cycloheptyl)-ethyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S14: (7E)-(1R,3R)-1,3-Bis-(tert-butyl-dimethyl-silanyloxy)-19-nor-9,10-secochola-5,7-dien-24-oic acid isopropyl ester as a colourless oil from (R)-4-[(1R,3aR,7aR)-7a-methyl-4-oxo-octahydro-inden-1-yl]-pentanoic acid isopropyl ester and (Z)-(3S,5R)-[2-[3,5-bis-(tert-butyl-dimethyl-silanyloxy)-2-methylene-cyclohexylidene]-ethyl]-diphenyl-phosphine oxide;

S15: (5Z,7E)-(1S,3R)-1,3-Bis-(tert-butyl-dimethyl-silanyloxy)-9,10-secochola-5,7,10 (19)-trien-24-oic acid 1-ethyl-propyl ester as a colourless oil from (R)-4-[(1R, 3aR,7aR)-7a-methyl-4-oxo-octahydro-inden-1-yl]pentanoic acid 1-ethyl-propyl ester and (Z)-(3S,5R)-[2-[3,5-bis-(tert-butyl-dimethyl-silanyloxy)-2-methylene-cyclohexylidene]-ethyl]-diphenyl-phosphine oxide;

S16: 2,2,-Dimethyl-propionic acid (7E)-(1R,3R,20R)-1,3-bis-(tert-butyl-dimethyl-silanyloxy)-20-methyl-19-nor-9,10-seco-pregna-5,7,16-triene-21-yl ester from 2,2-dimethyl-propionic acid (R)-2-[(3aR,7aS)-7a-methyl-4-oxo-3a,4,5,6,7,7a-hexahydro-3H-inden-1-yl]-propyl ester and -(3S,5R)-[2-[3,5-bis-(tert-butyl-dimethyl-silanyloxy)-cyclohexylidene]-ethyl]-diphenyl-phosphine oxide S17 (7E,22E)-(1R,3R)-1,3-Bis-(tert-butyl-dimethyl-silanyloxy)-19-nor-9,10-secocholan-5,7,22-trien-24-oic acid ethyl ester as a yellow oil from (E)-(R)-4-[(1R,3aR,7aR)-7a-methyl-4-oxo-octahydro-inden-1-yl]pent-2-enoic acid ethyl ester and [3S-(3alpha,5beta,Z)]-2-[2-[3,5-bis-[[(1,1-dimethylethyl)dimethyl-silyl]oxy]cyclohexylidene]ethyl]diphenyl phosphine oxide;

S18: (5Z,7E)-(1S,3R)-1,3-Bis-(tert-butyl-dimethyl-silanyloxy)-9,10-secochola-5,7-dien-24-oic acid ethyl ester as a colourless oil from (R)-4-[(1R,3aR,7aR)-7a-methyl-4-oxo-inden-1-yl]-pentanoic acid ethyl ester and (Z)-(3S,5R)-[2-[3,5-bis-(tert-butyl-dimethyl-silanyloxy)-2-methylene-cyclohexylidene]-ethyl]-diphenyl-phosphine oxide;

S19: 2,2-Dimethyl-propionic acid-(5Z,7E)-(1S,3R,20R)-1,3-bis-(tert-butyl-dimethyl-silanyloxy)-20-methyl-9,10-seco-pregna-5,7,10 (19)-trien-21-yl ester as a colourless foam from 2,2-Dimethyl-propionic acid (R)-2-[(1R,3aR,7aR)-7a-methyl-4-oxo-octahydro-inden-1-yl]propyl ester and (Z)-(3S,5R)-[2-[3,5-bis-(tert-butyl-dimethyl-silanyloxy)-2-methylene-cyclohexylidene]-ethyl]-diphenyl-phosphine oxide;

S20: 2-Methyl-2-trimethylsilanyloxy-propionic acid-(5Z,7E)-(1S,3R,20R)-1,3-bis-(tert-butyl-dimethyl-silanyloxy)-20-methyl-9,10-seco-pregna-5,7,10 (19)-trien-21-yl ester as a yellow oil from 2-methyl-2-trimethylsilanyloxy-propionic acid-(R)-2-[(1R,3aR,7aR)-7a-methyl-4-oxo-octahydro-inden-1-yl]propyl-ester and (Z)-(3S,5R)-[2-[3,5-bis-(tert-butyl-dimethyl-silanyloxy)-2-methylene-cyclohexylidene]-ethyl]-diphenyl-phosphine oxide;

S21: 2-Methyl-2-trimethylsilanyloxy-propionic acid-(5Z,7E)-(1R,3R,20R)-1,3-bis-(tert-butyl-dimethyl-silanyloxy)-20-methyl-19-nor-9,10-seco-pregna-5,7-dien-21-yl ester as a colourless oil from 2-methyl-2-trimethylsilanyloxy-propionic acid-(R)-2-[(1R,3aR,7aR)-7a-methyl-4-oxo-octahydro-inden-1-yl]propyl-ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S22: 2,2-Dimethyl-propionic acid-(5Z,7E)-(1S,3R,20S)-1,3-bis-(tert-butyl-dimethyl-silanyloxy)-20-methyl-9,10-seco-pregna-5,7,10 (19)-trien-21-yl ester as a colourless foam from 2,2-Dimethyl-propionic acid (S)-2-[(1R,3aR,7aR)-7a-methyl-4-oxo-octahydro-inden-1-yl]propyl ester and (Z)-(3S,5R)-[2-[3,5-bis-(tert-butyl-dimethyl-silanyloxy)-2-methylene-cyclohexylidene]-ethyl]-diphenyl-phosphine oxide;

S23: 2-Ethyl-2-trimethylsilanyloxy-butyric acid-(5Z,7E)-(1S,3R,20S)-1,3-bis-(tert-butyl-dimethyl-silanyloxy)-20-methyl-9,10-seco-pregna-5,7,10 (19)-trien-21-yl ester as a colourless oil from 2-Ethyl-2-trimethylsilanyloxy-butyric acid-(S)-2-[(1R,3aR,7aR)-7a-methyl-4-oxo-octahydro-inden-1-yl]propyl ester and (Z)-(3S,5R)-[2-[3,5-bis-(tert-butyl-dimethyl-silanyloxy)-2-methylene-cyclohexylidene]-ethyl]-diphenyl-phosphine oxide;

S24 2-Methyl-2-trimethylsilanyloxy-propionic acid-(7E)-(1R,3R,20S)-1,3-bis-(tert-butyl-dimethyl-silanyloxy)-20-methyl-19-nor-9,10-seco-pregna-5,7-dien-21-yl ester as a yellow oil from 2-methyl-2-trimethylsilanyloxy-propionic acid(S)-2-[(1R,3aR,7aR)-7a-methyl-4-oxo-octahydro-inden-1-yl]-propyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S25: 2-Ethyl-2-trimethylsilanyloxy-butyric acid-(7E)-(1R,3R,20S)-1,3-bis-(tert-butyl-dimethyl-silanyloxy)-20-methyl-19-nor-9,10-seco-pregna-5,7-dien-21-yl ester as a colourless oil from 2-Ethyl-2-trimethylsilanyloxy-butyric acid-(S)-2-[(1R,3aR,7aR)-7a-methyl-4-oxo-octahydro-inden-1-yl]propyl ester and [3S-(3alpha,5beta,Z)]-2-[2-[3,5-bis-[[(1,1-dimethylethyl)dimethylsilyl]oxy]cyclohexylidene]ethyl]diphenyl phosphine oxide;

S26: 5Z,7E)-(1S,3R)-1,3-Bis-(tert-butyl-dimethyl-silanyloxy)-9,10-seco-androsta-5,7,10 (19)-triene-17b-carboxylic acid 3-methyl 3-trimethylsilanyloxy-butyl ester from (1S,3aR,7aS)-7a-methyl-4-oxo-octahydroindene-1-carboxylic acid 3-methyl-3-trimethylsilanyloxy-butyl ester and (3S,5R)-[2-[3,5-bis-(tert-butyldimethyl-silanyloxy)-cyclohexylidene]-ethyl]-diphenyl-phosphine oxide S27: (7E)-(1R,3R)-1,3-Bis-(tert-butyl-dimethyl-silanyloxy)-19-nor-9,10-seco-androsta-5,7-diene-17b-carboxylic acid 3-methyl 3-trimethylsilanyloxy-butyl ester from (1S,3aR,7aS)-7a-methyl-4-oxo-octahydroindene-1-carboxylic acid 3-methyl-3-trimethylsilanyloxy-butyl ester and (Z)-(3S,5R)-[2-[3,5-bis-(tert-butyl-dimethyl-silanyloxy)-2-methylene-cyclohexylidene]-ethyl]-diphenyl-phosphine oxide The compounds of formula I can be used in the treatment of dermatological conditions, particularly psoriasis. In contradistinction to vitamin D derivatives such as calcitriol which have been proposed earlier for the treatment of psoriasis the compounds of formula I exert no or only minor systemic activity when applied topically. Thus, unwanted effects such as loss of body weight or calcium deposits in the kidney which have been observed in the treatment of psoriasis using known vitamin D derivatives can be avoided or substantially reduced by topical application of a compound of formula I.

In accordance with this invention, the compounds of formula I can be provided in pharmaceutically acceptable, preferably topical compositions. These pharmaceutical compositions of the invention contain a compound of formula I in association with a compatible pharmaceutically acceptable carrier material. Any conventional carrier material can be utilized. The carrier material can be an organic or inorganic inert carrier material suitable for topical administration such as solutions, suspensions, ointments, creams, gels, micronized powders, aerosols and the like. The pharmaceutical preparations may be sterilized and/or may contain adjuvants such as preservatives, stabilizers, wetting agents, emulsifiers, salts for varying the osmotic pressure and/or buffers. Among the preferred methods of applying the composition containing the agents of this invention is in the form of a gel, lotion and cream. The pharmaceutical preparation for topical administration to the skin can be prepared by mixing the aforementioned active ingredient with non-toxic, therapeutically inert, solid or liquid carriers customarily used in such preparations. These preparations should contain at least about 1 $\mu$g of the active ingredient per g of the composition. It is preferred that these preparations contain about 0.001 to 0.015% percent by weight of the active ingredient based upon the total weight of the composition. It is also preferred to apply these preparations once or twice daily to the skin. These preparations can be applied according to the need of the patient.

In preparing the topical preparations described above additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the aforementioned active agent. Among the conventional antioxidants which can be utilized in these preparations are included N-methyl-a-tocopherolamine, tocopherols, butylated hydroxyanisole, butylated hydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, 1,2-ethyleneglycol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of a fatty acid alcohol, a semi-solid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are derived from the reduction of a long-chain saturated fatty acid of at least about 14 carbon atoms. Also, conventional perfumes and lotions generally utilized in topical preparation for the hair can be utilized in accordance with this invention. Furthermore, if desired, conventional emulsifying agents can be utilized in the topical preparations of this invention.

The pharmacological properties of the compounds of the formula I were determined by the following test procedures:
1. VDR activation In order to measure the activation of the vitamin D receptor (VDR) by vitamin D analogs in cells a transcription activation assay was used. COS cells were cotransfected with the human VDR (expressed in pSG5) and a reporter gene containing three response elements (VDRE3) from the rat osteocalcin gene, the thymidine kinase basal promoter, and the luciferase reporter gene.

In this system, the activity of the test compound is expressed as the concentration which leads to an 8–10 fold induction of the luciferase activity with half-maximal activity ($ED_{50}$).
2. Calcium liability (tolerance test in mice)

This routine test gives a global picture of calcemic liability. Profound changes in calcium homeostasis strongly affect the weight development of the animals. This parameter was used as a primary test for tolerance. Mice (25–30 g body weight.) received daily subcutaneous administrations of the vitamin D derivative for 4 consecutive days. Body weight was registered just before and at the end of a 5 day treatment period. The "highest tolerated dose" (HTD) in mice is the dose which results in zero weight gain during this treatment period.

The results obtained with the compounds of the formula I in these test procedures are shown in Table 1

TABLE 1

| Compound of Example No. | Vitamin D Receptor Activation $ED_{50}$ [nM] | HTD in mice [μg/kg] |
| --- | --- | --- |
| 7 | 18 | >5000 |
| 8 | 38 | 1000 |
| 9 | 5.6 | 1000 |
| 10 | 31 | >6000 |
| 11 | 180 | >6000 |
| 19 | 0.28 | >6000 |
| 20 | 0.82 | >10000 |
| 21 | 0.55 | >9000 |
| 22 | 141 | 9000 |
| 23 | 83 | >11000 |
| 24 | 18 | 2500 |
| 28 | 0.53 | 500 |
| 29 | 2.5 | 7000 |
| Calcitriol | 2.8 | 0.5 |

The following Examples illustrate the invention further.

EXAMPLE 1

(7E)-(1R,3R,20S)-1,3-Bis-(tert-butyl-dimethyl-silanyloxy)-20-methyl-19-nor-9,10-seco-pregna-5,7-dien-21-oic acid cyclopropylmethyl ester (239.5 mg, 0.38 mmole) was dissolved in ethylacetate (3.8 ml) and acetonitrile (7.6 ml); aqu. HF (0.38 ml) was added; the reaction mixture was stirred at ambient temperature for one hour. After addition of water (8.0 ml) and sat. aqu. NaHCO3 (8.0 ml) the mixture was extracted with ethyl acetate (10.0 ml and 2×5.0 ml); the combined organic layers were washed with sat. aqu. NaCl (10.0 ml) and dried over MgSO4. After filtration the solvent was removed in vacuo; the crude product was chromatographed on silica gel (ethyl acetate : 2-propanol—95:05).

(7E)-(1R,3R,20S)-1,3-Dihydroxy-20-methyl-19-nor-9,10-seco-pregna-5,7-dien-21-oic acid cyclopropylmethyl ester was obtained as colourless solid;

MS (EI): $^m/_e$=402 (M$^{·+}$), 55 (100)

IR (KBr): 3387, 2947, 2876, 2844, 1731, 1158, 1048, 975 cm$^{-1}$

In analogy, the following compounds were prepared (Examples 2–32):

EXAMPLE 2

(7E)-(1R,3R,20S)-1,3-Dihydroxy-20-methyl-19-nor-9,10-seco-pregna-5,7-dien-21-oic acid cyclopentylmethyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid cyclopentylmethyl ester MS (EI): $^m/_e$=430 (M$^{·+}$), 180 (56), 133 (66), 81 (60), 55 (100), 41 (72)

IR (KBr): 3426, 2948, 2872, 1731, 1453, 1159, 1047, 976 cm$^{-1}$

EXAMPLE 3

(7E)-(1R,3R,20S)-1,3-Dihydroxy-20-methyl-19-nor-9,10-seco-pregna-5,7-dien-21-oic acid cyclohexylmethyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid cyclohexylmethyl ester MS (EI): $^m/_e$=444 (M$^{·+}$), 180 (40), 133 (38), 97 (43), 55 (100), 41 (37)

IR (KBr): 3406, 2929, 2876, 2851, 1733, 1447, 1159, 1049 cm$^{-1}$

EXAMPLE 4

(7E)-(1R,3R,20S)-1,3-Dihydroxy-20-methyl-19-nor-9, 10-seco-pregna-5,7-dien-21-oic acid (1S,2S,5S)-6,6- dimethyl-bicyclo[3.1.1]hept-2-ylmethyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid (1S,2S,5S)-6,6-dimethyl-bicyclo[3.1.1]hept-2-ylmethyl ester MS (EI): $m/e$=484 (M$^{*+}$), 137 (28), 95 (38), 81 (100), 69 (47)

IR (KBr): 3437, 2940, 2872, 1732, 1458, 1157, 1049 cm$^{-1}$

EXAMPLE 5

(7E)-(1R,3R,20S)-1,3-Dihydroxy-20-methyl-19-nor-9,10-seco-pregna-5,7-dien-21-oic acid (1S,2R,5S)-6,6-dimethyl-bicyclo[3.1.1]hept-2-ylmethyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid (1S,2R,5S)-6,6-dimethyl-bicyclo[3.1.1]hept-2-ylmethyl ester MS (EI): $m/e$=484 (M$^{*+}$), 137 (31), 95 (42), 81 (100), 69 (54)

IR (KBr): 3433, 2942, 2876, 1731, 1457, 1156, 1047 cm$^{-1}$

EXAMPLE 6

(7E)-(1R,3R,20S)-1,3-Dihydroxy-20-methyl-19-nor-9,10-seco-pregna-5,7-dien-21-oic acid (1R,5S)-6,6-dimethyl-bicyclo[3.1.1]hept-2-en-2-ylmethyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid (1R,5S)-6,6-dimethyl-bicyclo[3.1.1]hept-2-en-2-ylmethyl ester MS (EI): $m/e$=482 (M$^{*+}$), 207 (42), 135 (59), 107 (63), 93 (100), 79 (70), 69 (33), 55 (42), 43 (43)

IR (KBr): 3415, 2942, 2876, 1737, 1438, 1378, 1246, 1204, 1170, 1048 cm$^{-1}$

EXAMPLE 7

(7E)-(1R,3R,20S)-1,3-Dihydroxy-20-methyl-19-nor-9,10-seco-pregna-5,7-dien-21-oic acid 1-hydroxy-cyclopentylmethyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid 1-triethylsilanyloxy-cyclopentylmethyl ester MS (EI): $m/e$=446 (M$^{*+}$), 133 (46), 95 (40), 81 (100), 69 (30), 55 (40), 41 (41)

IR (KBr): 3406, 2945, 2876, 1734, 1155, 1045, 978 cm$^{-1}$

EXAMPLE 8

(7E)-(1R,3R,20S)-1,3-Dihydroxy-20-methyl-19-nor-9,10-seco-pregna-5,7-dien-21-oic acid 1-hydroxy-cyclohexyl methyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid 1-triethylsilanyloxy-cyclohexylmethyl ester MS (EI): $m/e$=460(M$^{*+}$), 133 (45), 95 (100), 81 (51), 55 (54), 41 (35)

IR (KBr): 3424, 2935, 2873, 1732, 1451, 1159, 1047, 972 cm$^{-1}$

EXAMPLE 9

(5Z,7E)-(1R,3R,20S)-1,3-Dihydroxy-20-methyl-9,10-seco-pregna-5,7,10-trien-21-oic acid 1-hydroxy-cyclohexylmethyl ester as a colourless foam from (5Z,7E)-(1R,3R,20S)-1,3-Bis-(tert-butyl-dimethyl-silanyloxy)-20-methyl-9,10-seco-pregna-5,7,10-trien-21-oic acid 1-triethylsilanyloxy-cyclohexylmethyl ester MS (EI): $m/e$=472(M$^{*+}$), 134 (69), 95 (100), 81 (33), 55 (24), 41 (25)

IR (neat): 3419, 2937, 2873, 1732, 1444, 1379, 1262, 1160, 1055, 964, 917 cm$^{-1}$

EXAMPLE 10

(7E)-(1R,3R,20S)-1,3-Dihydroxy-20-methyl-19-nor-9,10-seco-pregna-5,7-dien-21-oic acid 1-hyddroxy-cycloheptylmethyl ester as a colourless oil from (7E)-(1R,3R,20S)-1,3-Bis-(tert-butyl-dimethyl-silanyloxy)-20-methyl-19-nor-9,10-seco-pregna-5,7-dien-21-oic acid 1-triethylsilanyloxy-cycloheptylmethyl ester MS (EI): $m/e$=474(M$^{*+}$), 133 (64), 109 (87), 55 (88)

IR (neat): 3400, 2930, 2874, 1730, 1456, 1379, 1261, 1161, 1046 cm$^{-1}$

EXAMPLE 11

(7E)-(1R,3R,20S)-1,3-Dihydroxy-20-methyl-19-nor-9,10-seco-pregna-5,7-dien-21-oic acid 2-(1-hyddroxy-cyclopentyl)-ethyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid 2-(1-triethylsilanyloxy-cyclopentyl)-ethyl ester MS (EI): $m/e$=460(M$^{*+}$), 180 (19), 133 (22), 95 (100), 55 (27)

IR (KBr): 3500, 3387, 2939, 2873, 1711, 1457, 1393, 1334, 1283, 1175, 1051 cm$^{-1}$

EXAMPLE 12

(7E)-(1R,3R,20S)-1,3-Dihydroxy-20-methyl-19-nor-9,10-seco-pregna-5,7-dien-21-oic acid 2-(1-hyddroxy-cyclohexyl)-ethyl ester as a colourless solid from (7E)-(1R,3R,20S)-1,3-Bis-(tert-butyl-dimethyl-silanyloxy)-20-methyl-19-nor- 9,10-seco-pregna-5,7-dien-21-oic acid 2-(1-triethylsilanyloxy-cyclohexyl)-ethyl ester MS (EI): $m/e$=474 (M$^{*+}$), 109 (100), 81 (30), 67 (35), 55 (28)

IR (KBr): 3430, 2933, 2872, 1729, 1710, 1452, 1263, 1162, 1047, 975 cm$^{-1}$

EXAMPLE 13

(7E)-(1R,3R,20S)-1,3-Dihydroxy-20-methyl-19-nor-9,10-seco-pregna-5,7-dien-21-oic acid 2-(1-hyddroxy-cycloheptyl)-ethyl ester as a colourless solid from (7E)-(1R,3R,20S)-1,3-Bis-(tert-butyl-dimethyl-silanyloxy)-20-methyl-19-nor-9,10-seco-pregna-5,7-dien-21-oic acid 2-(1-triethylsilanyloxy-cycloheptyl)-ethyl ester MS (EI): $m/e$=488 (M$^{*+}$), 123 (71), 81 (100), 67 (46), 55 (49), 41 (34)

IR (KBr): 3411, 2931, 2871, 1732, 1458, 1161, 1048, 977 cm$^{-1}$

EXAMPLE 14

(7E)-(1R,3R)-1,3-Dihydroxy-19-nor-9,10-seco-chola-5,7-dien-24-oic acid isopropyl ester as a colourless oil from (7E)-(1R,3R)-1,3-Bis-(tert-butyl-dimethyl-silanyloxy)-19-nor-9,10-seco-chola-5,7-dien-24-oic acid isopropyl ester.

MS: m/e=418 (M$^{*+}$)

IR (neat): 3373, 2930, 2874, 1731, 1450, 1375, 1260, 1216, 1178, 1108, 1048, 978, 810 cm$^{-1}$.

EXAMPLE 15

(5Z,7E)-(1R,3R)-1,3-Dihydroxy-9,10-seco-chola-5,7,10 (19)-trien-24-oic acid 1-ethyl-propyl ester as a yellow oil from (5Z,7E)-(1S,3R)-1,3-Bis-(tert-butyl-dimethyl-silanyloxy)-9,10-seco-chola-5,7,10 (19)-trien-24-oic acid 1-ethyl-propyl ester MS: m/e=458 (M$^{.+}$)

IR (neat): 3361, 2942, 2876, 1731, 1458, 1380, 1259, 1219, 1171, 1098, 1054, 956, 897 cm$^{-1}$.

EXAMPLE 16

2,2-Dimethyl-propionic acid (7E)-(1R,3R,20R)-1.3-dihydroxy-20-methyl-19-nor-9,10-seco-pregna-5,7,17-trien-21-yl ester as a colourless solid from 2,2,-Dimethyl-propionic acid (7E)-(1R,3R,20R)-1,3-bis-(tert-butyl-dimethyl-silanyloxy)-20-methyl-19-nor-9,10-seco-pregna-5,7,16-triene-21-yl ester MS (EI): $^m/_e$=416 (M$^{.+}$)

IR (neat): 3397, 2931, 1728 cm$^{-1}$

EXAMPLE 17

(7E,22E)-(1R,3R)-1,3-Dihydroxy-19-nor-9,10-secocholan-5,7,22-trien-24-oic acid ethyl ester colourless solid from (7E,22E)-(1R,3R)-1,3-Bis-(tert-butyl-dimethyl-silanyloxy)-19-nor-9,10-secocholan-5,7,22-trien-24-oic acid ethyl ester.

MS: m/e=402 (M$^{.+}$)

IR (KBr): 3351, 2958, 2931, 2873, 1717, 1650, 1456, 1369, 1334, 1272, 1235, 1198, 1178, 1143, 1094, 1037, 982 cm$^{-1}$.

EXAMPLE 18

(5Z,7E)-(1S,3R)-1,3-Dihydroxy-9,10-secochola-5,7-dien-24-oic acid ethyl ester as a colourless foam from (5Z,7E)-(1S,3R)-1,3-Bis-(tert-butyl-dimethyl-silanyloxy)-9,10-secochola-5,7-dien-24-oic acid ethyl ester MS: m/e=416 (M$^{.+}$)

IR (KBr): 3425, 2945, 2873, 1736, 1446, 1376, 1298, 1255, 1218, 1183, 1096, 1055 cm$^{-1}$.

EXAMPLE 19

2,2-Dimethyl-propionic acid-(5Z,7E)-(1S,3R,20R)-1,3-dihydroxy-20-methyl-9,10-seco-pregna-5,7,10 (19)-trien-21-yl ester as a colourless foam from 2,2-Dimethyl-propionic acid-(5Z,7E)-(1S,3R,20R)-1,3-bis-(tert-butyl-dimethyl-silanyloxy)-20-methyl-9,10-seco-pregna-5,7,10 (19)-trien-21-yl ester.

MS: m/e=430 (M$^{.+}$)

IR (KBr): 3431, 2960, 2933, 2873, 1728, 1634, 1479, 1457, 1399, 1364, 1286, 1164, 1054 cm$^{-1}$

EXAMPLE 20

2-Hydroxy-2-methyl-propionic acid-(5Z,7E)-(1S,3R,20R)-1,3-dihydroxy-20-methyl-9,10-seco-pregna-5,7,10 (19)-trien-21-yl ester as a colourless solid from 2-methyl-2-trimethylsilanyloxy-propionic acid-(5Z,7E)-(1S,3R,20R)-1,3-bis-(tert-butyl-dimethyl-silanyloxy)-20-methyl-9,10-seco-pregna-5,7,10 (19)-trien-21-yl ester MS: m/e=432 (M$^{.+}$)

IR (KBr): 3427, 2934, 2874, 1729, 1467, 1380, 1274, 1162, 1055 cm$^{-1}$.

EXAMPLE 21

2-Hydroxy-2-methyl-propionic acid-(7E)-(1R,3R,20R)-1,3-dihydroxy-20-methyl-19-nor-9,10-seco-pregna-5,7-dien-21-yl ester as a colourless solid from 2-methyl-2-trimethylsilanyloxy-propionic acid-(5Z,7E)-(1R,3R,20R)-1,3-bis-(tert-butyl-dimethyl-silanyloxy)-20-methyl-19-nor-9,10-seco-pregna-5,7-dien-21-yl ester MS: m/e=420 (M$^{.+}$)

IR (KBr): 3424, 2936, 2875, 1729, 1460, 1380, 1273, 1160, 1048, 976 cm$^{-1}$

EXAMPLE 22

2,2-Dimethyl-propionic acid (5Z,7E)-(1R,3R)-1,3-dihydroxy-23,24-dinor-9,10-secochola-5,7-dien-22-yl ester from 2,2-Dimethyl-propionic acid-(5Z,7E)-(1S,3R,20S)-1,3-bis-(tert-butyl-dimethyl-silanyloxy)-20-methyl-9,10-seco-pregna-5,7,10 (19)-trien-21-yl ester MS: m/e=430 (M$^{.+}$)

IR (KBr): 3443, 2946, 2874, 1729, 1702, 1478, 1399, 1292, 1164, 1053 cm$^{-1}$

EXAMPLE 23

2-Hydroxy-2-methyl-propionic acid-(5Z,7E)-(1S,3R,20S)-1,3-dihydroxy-20-methyl-9,10-seco-pregna-5,7,10 (19)-trien-21-yl ester as a colourless solid from 2-methyl-2-trimethylsilanyloxy-propionic acid-(5Z,7E)-(1S,3R,20S)-1,3-bis-(tert-butyl-dimethyl-silanyloxy)-20-methyl-9,10-seco-pregna-5,7,10 (19)-trien-21-yl ester MS: m/e=432 (M$^{.+}$)

IR (KBr): 3435, 2945, 2875, 1727, 1468, 1378, 1275, 1164, 1054, 957 cm$^{-1}$.

EXAMPLE 24

2-Ethyl-2-hydroxy-butyric acid-(5Z,7E)-(1S,3R,20S)-1,3-dihydroxy-20-methyl-9,10-seco-pregna-5,7,10 (19)-trien-21-yl ester colourless foam from 2-Ethyl-2-trimethylsilanyloxy-butyric acid-(5Z,7E)-(1S,3R,20S)-1,3-bis-(tert-butyl-dimethyl-silanyloxy)-20-methyl-9,10-seco-pregna-5,7,10 (19)-trien-21-yl ester MS: m/e=460 (M$^{.+}$)

IR (KBr): 3427, 2943, 2877, 1725, 1460, 1378, 1235, 1167, 1054, 986, 956 cm$^{-1}$.

EXAMPLE 25

2-Hydroxy-2-methyl-propionic acid(7E)-(1R,3R,20S)-1,3-dihydroxy-20-methyl-19-nor-9,10-seco-pregna-5,7-dien-21-yl ester as a colourless solid from 2-methyl-2-trimethylsilanyloxy-propionic acid-(7E)-(1R,3R,20S)-1,3-bis-(tert-butyl-dimethyl-silanyloxy)-20-methyl-19-nor-9,10-seco-pregna-5,7-dien-21-yl ester MS: m/e=420 (M$^{.+}$)

IR (KBr): 3403, 2941, 2877, 2826, 1747, 1453, 1416, 1361, 1273, 1205, 1145, 1051, 977 cm$^{-1}$

EXAMPLE 26

2-Ethyl-2-hydroxy-butyric acid (7E)-(1R,3R,20S)-1,3-dihydroxy-20-methyl-19-nor-9,10-seco-pregna-5,7-dien-21-yl ester as a colourless foam from 2-Ethyl-2-trimethylsilanyloxy-butyric acid-(7E)-(1R,3R,20S)-1,3-bis-(tert-butyl-dimethyl-silanyloxy)-20-methyl-19-nor-9,10-seco-pregna-5,7-dien-21-yl ester.

MS: m/e=448 (M$^{.+}$)

IR (KBr): 3545, 3372, 2942, 2877, 1721, 1457, 1378, 1337, 1293, 1229, 1159, 1091, 1052, 987, 808 cm$^{-1}$

EXAMPLE 27

3-Methyl-butyric acid 2-[(1S,3R,20S)-1,3-dihydroxy-20-methyl-9,10-seco-pregna-5,7,10 (19)-trien-21-yl]-propyl ester as a colourless foam from 3-methyl-butyric acid (5Z, 7E)-2-[(1S,3R,20S)-1,3-bis-(tert-butyl-dimethyl-silanyloxy)-20-methyl-9,10-seco-pregna-5,7,10 (19)-trien-21-yl]-propyl ester MS: m/e=430 (M$^{\cdot+}$)

IR (KBr): 3426, 2955, 2874, 1735, 1466, 1371, 1296, 1257, 1190, 1055 cm$^{-1}$

EXAMPLE 28

2-Hydroxy-2-methyl-propionic acid-(5Z,7E)-(1S,3R, 20S)-1,3-dihydroxy-20-methyl-9,10-seco-pregna-5,7,10 (19)-trien-21-yl ester as a colourless solid from 1:1 mixture of (R)-and-(S)-2-Hydroxy-2-trifluoromethyl-butyric acid-(5Z,7E)-(1S,3R,20S)-1,3-bis-(tert-butyl-dimethyl-silanyloxy)-20-methyl-9,10-seco-pregna-5,7,10 (19)-trien-21-yl ester MS: m/e=500 (M)

IR (KBr): 3428, 2948, 2875, 1721, 1380, 1345, 1294, 1168, 1098, 1054 cm$^{-1}$.

EXAMPLE 29

1:1 Mixture of (R)-and-(S)-3-hydroxy-3-methyl-pentanoic acid-(5Z,7E)-(1S,3R,20S)-1,3-dihydroxy-20-methyl-9,10-seco-pregna-5,7,10 (19)-trien-21-yl ester as a colourless foam from 1:1 Mixture of (R)-and-(S)-3-hydroxy-3-methyl-pentanoic acid-(5Z,7E)-(1S,3R,20S)-1, 3-bis-(tert-butyl-dimethyl-silanyloxy)-20-methyl-9,10-seco-pregna-5,7,10 (19)-trien-21-yl ester MS: m/e=328 (M-.O$_2$CC$_5$H$_{13}$OH)

IR (KBr): 3425, 2944,2877, 1713, 1458, 1377, 1330, 1204, 1144, 1054, 989 cm$^{-1}$

EXAMPLE 30

2-Hydroxy-2-methyl-propionic acid (7E)-(1R,3R,20R)-1.3-dihydroxy-20-methyl-19-nor-9,10-seco-pregna-5,7,17-trien-21-yl ester as a colourless solid from 2-Hydroxy-2-methyl-propionic acid (7E)-(1R,3R,20R)-1,3-bis-(tert-butyl-dimethyl-silanyloxy)-20-methyl-19-nor-9,10-seco-pregna-5,7,16-triene-21-yl ester MS (EI): $^m/_e$=418 (M$^{\cdot+}$)

EXAMPLE 31

(7E)-(1R,3R)-1,3-Dihydroxy-19-nor-9,10-seco-androsta-5,7-diene-17b-carboxylic acid 3-hydroxy-3-methyl-butyl ester as a colourless foam from (7E)-(1R,3R)-1,3-Bis-(tert-butyl-dimethyl-silanyloxy)-19-nor-9,10-seco-androsta-5,7-diene-17b-carboxylic acid 3-methyl 3-trimethylsilanyloxy-butyl ester MS (EI): m/e=406 (M$^{\cdot+}$)

IR (neat): 3412, 2932, 2879, 1726 cm$^{-1}$

EXAMPLE 32

(5Z,7E)-(1S,3R)-1,3-Dihydroxy-9,10-seco-androsta-5,7, 10(19)-triene-17b-carboxylic acid 3-hydroxy-3-methyl-butyl ester as a colourless solid from (5Z,7E)-(1S,3R)-1,3-Bis-(tert-butyl-dimethyl-silanyloxy)-9,10-seco-androsta-5, 7,10(19)-triene-17b-carboxylic acid 3-methyl 3-trimethylsilanyloxy-butyl ester MS (EI): $^m/_e$=418 (M$^{\cdot+}$)

IR (neat): 3424, 2987, 2932, 2879 cm$^{-1}$

EXAMPLE A

| Cream Compound of formula I 0.001–1 mg/g | |
|---|---|
| | Gew. % |
| Cetyl alcohol | 1.5 |
| Stearyl alcohol | 2.5 |
| Sorbitan monostearate | 2.0 |
| Glyceryl monostearate and polyoxyethylene glycolstearate | 4.0 |
| Polysorbate 60 | 1.0 |
| Mineral oil | 4.0 |
| Propylene glycol | 5.0 |
| Propylparaben | 0.05 |
| Butylated hydroxyanisole | 0.05 |
| Sorbitol solution | 2.0 |
| Na EDTA | 0.01 |
| Methylparaben | 0.18 |
| Dist. water q.s. ad | 100.00 |

We claim:

1. A method of treating dermatological conditions comprising topically administering to a host in need of such treatment an effective amount of a compound of formula I

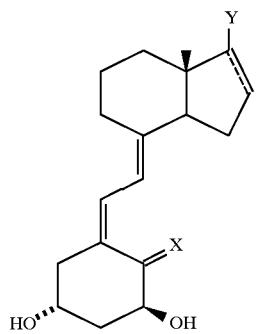

wherein

X is =CH$_2$ or H,H;

Y is

—CH(CH$_3$)—(A)$_n$—C(O)—OR$^1$      (a)

—CH(CH$_3$)—CH$_2$—O—C(O)R$^2$      (b)

or

—C(O)—OR$^1$      (c);

A is —CH=CH— or CH$_2$—CH$_2$—

R$^1$ is lower alkyl, cycloalkyl, cycloalkylmethyl, —CH$_2$R$^3$ or —CH$_2$—CH$_2$R$^3$;

R$^2$ is lower alkyl, cycloalkyl or R$^3$;

R$^3$ is hydroxy-lower alkyl, hydroxy-cycloalkyl or trifluoromethyl-hydroxy-lower-alkyl;

n is 0 or 1; and the dotted bond in the five-membered ring is optional.

2. A compound of formula

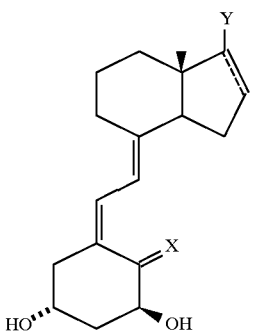

wherein

X is =CH$_2$ and Y is

—CH(CH$_3$)—CH$_2$—O—C(O)R$^2$  (b)

or

—C(O)—OR$^1$  (c);

or

X is H,H and Y is

—CH(CH$_3$)—(A)$_n$—C(O)—OR$^1$  (a)

—CH(CH$_3$)—CH$_2$—O—C(O)R$_2$  (b)

or

—C(O)—OR$^1$  (c);

A is —CH=CH— or CH$_2$—CH$_2$—

R$^1$ is lower alkyl, cycloalkyl, cycloalkylmethyl, —CH$_2$R$^3$ or —CH$_2$—CH$_2$R$^3$, R$^2$ is lower alkyl, cycloalkyl or R$^3$, R$^3$ is hydroxy-lower alkyl, hydroxy-cycloalkyl or trifluoromethyl-hydroxy-lower-alkyl;

n is 0 or 1;

with the proviso that X is H,H when Y is —CH(CH$_3$)—CH$_2$—OC(O)—C(OH)(CH$_3$)$_2$ and the dotted bond in the five-membered ring is absent.

3. A compound according to claim 2, wherein X is =CH$_2$ and Y is

—CH(CH$_3$)—CH$_2$—O—C(O)—R$^2$  (b)

or

—C(O)—OR$^1$  (c).

4. A compound according to claim 2, wherein Y is CH(CH$_3$)—CH$_2$—O—C(O)—R$^2$ (b) and X is =CH$_2$ or H,H.

5. The compound according to claim 4, 2,2-Dimethyl-propionic acid-(5Z,7E)-(1S,3R,20R)-1,3-dihydroxy-20-methyl-9,10-seco-pregna-5,7,10 (19)-trien-21-yl ester 2-Hydroxy-2-methyl-propionic acid-(5Z,7E)-(1S,3R, 20R)-1,3-dihydroxy-20-methyl-9,10-seco-pregna-5,7,10 (19)-trien-21-yl ester 2,2-Dimethyl-propionic acid (5Z,7E)-(1R,3R)-1,3-dihydroxy-23,24-dinor-9,10-secochola-5,7-dien-22-yl ester 2-Ethyl-2-hydroxy-butyric acid-(5Z,7E)-(1S,3R,20S)-1,3-dihydroxy-20-methyl-9,10-seco-pregna-5,7,10 (19)-trien-21-yl ester 3-Methyl-butyric acid 2-[(1S,3R,20S)-1,3-dihydroxy-20-methyl-9,10-seco-pregna-5,7,10 (19)-trien-21-yl]-propyl ester 2-Hydroxy-2-methyl-propionic acid-(5Z,7E)-(1S,3R, 20S)-1,3-dihydroxy-20-methyl-9,10-seco-pregna-5, 7,10 (19)-trien-21-yl ester 1:1 Mixture of (R)-and-(S)-3-hydroxy-3-methylpentanoic acid-(5Z,7E)-(1S,3R,20S)-1,3-dihydroxy-20-methyl-9,10-seco-pregna-5,7,10 (19)-trien-21-yl ester.

6. A compound according to claim 3 wherein Y is C(O)—OR$^1$— (c).

7. The compound of claim 6, (5Z,7E)-(1S,3R)-1,3-dihydroxy-9,10-seco-androsta-5,7,10(19)triene-17b-carboxylic acid 3-hydroxy-3-methyl-butyl ester.

8. A compound according to claim 2, wherein X is H,H and Y is

—CH(CH$_3$)—(A)$_n$—C(O)—OR$^1$  (a)

—CH(CH$_3$)—CH$_2$—O—C(O)—R$^2$  (b)

or

—C(O)—OR$^1$  (c).

9. A compound according to claim 8 wherein Y is CH(CH$_3$)—(A)$_n$—C(O)—OR$^1$ (a).

10. The compound according to claim 9, (7E)-(1R,3R,20S)-1,3-Dihydroxy-20-methyl-19-nor-9, 10-seco-pregna-5,7-dien-21-oic acid cyclopropylmethyl ester (7E)-(1R,3R,20S)-1,3-Dihydroxy-20-methyl-19-nor-9, 10-seco-pregna-5,7-dien-21-oic acid cyclopentylmethyl ester (7E)-(1R,3R,20S)-1,3-Dihydroxy-20-methyl-19-nor-9, 10-seco-pregna-5,7-dien-21-oic acid cyclohexylmethyl ester (7E)-(1R,3R,20S)-1,3-Dihydroxy-20-methyl-19-nor-9, 10-seco-pregna-5,7-dien-21-oic acid (1S,2S,5S)-6,6-dimethyl-bicyclo[3.1.1]hept-2-ylmethyl ester (7E)-(1R,3R,20S)-1,3-Dihydroxy-20-methyl-19-nor-9, 10-seco-pregna-5,7-dien-21-oic acid (1S,2R,5S)-6,6-dimethyl-bicyclo[3.1.1]hept-2-ylmethyl ester (7E)-(1R,3R,20S)-1,3-Dihydroxy-20-methyl-19-nor-9, 10-seco-pregna-5,7-dien-21-oic acid (1R,5S)-6,6-dimethyl-bicyclo[3.1.1]hept-2-en-2-ylmethyl ester (7E)-(1R,3R,20S)-1,3-Dihydroxy-20-methyl-19-nor-9, 10-seco-pregna-5,7-dien-21-oic acid 1-hydroxy-cyclopentylmethyl ester (7E)-(1R,3R,20S)-1,3-Dihydroxy-20-methyl-19-nor-9, 10-seco-pregna-5,7-dien-21-oic acid 1-hydroxy-cyclohexyl methyl ester (7E)-(1R,3R,20S)-1,3-Dihydroxy-20-methyl-19-nor-9, 10-seco-pregna-5,7-dien-21-oic acid 1-hyddroxy-cycloheptylmethyl ester (7E)-(1R,3R,20S)-1,3-Dihydroxy-20-methyl-19-nor-9, 10-seco-pregna-5,7-dien-21-oic acid 2-(1-hydroxy-cyclopentyl)-ethyl ester (7E)-(1R,3R,20S)-1,3-Dihydroxy-20-methyl-19-nor-9, 10-seco-pregna-5,7-dien-21-oic acid 2-(1-hyddroxy-cyclohexyl)-ethyl ester (7E)-(1R,3R,20S)-1,3-Dihydroxy-20-methyl-19-nor-9, 10-seco-pregna-5,7-dien-21-oic acid 2-(1-hyddroxy-cycloheptyl)-ethyl ester (7E)-(1R,3R)-1,3-Dihydroxy-19-nor-9,10-seco-chola-5,7-dien-24-oic acid isopropyl ester (7E,22E)-(1R,3R)-1,3-Dihydroxy-19-nor-9,10-secocholan-5,7,22-trien-24-oic acid ethyl ester.

11. A compound according to claim 8 wherein Y is CH(CH$_3$)—CH$_2$—O—C(O)R$^2$ (b).

12. A compound according to of claim 11, 2,2-Dimethyl-propionic acid (7E)-(1R,3R,20R)-1.3-dihydroxy-20-methyl-19-nor-9,10-seco-pregna-5,7,17-trien-21-yl ester 2-Hydroxy-2-methyl-propionic acid-(7E)-(1R,3R,20R)-1,3-dihydroxy-20-methyl-19-nor-9,10-seco-pregna-5,7-dien-21-yl ester 2-Hydroxy-2-methyl-propionic acid(7E)-(1R,3R,20S)-1,3-dihydroxy-20-methyl-19-nor-9,10-seco-pregna-5,7-dien-21-yl ester 2-Ethyl-2-hydroxy-butyric acid (7E)-(1R,3R,20S)-1,3-dihydroxy-20-methyl-19-nor-9,10-seco-pregna-5,7-trien-21-yl ester or 2-Hydroxy-2-methyl-propionic acid (7E)-(1R,3R,20R)-1.3-dihydroxy-20-methyl-19-nor-9,10-seco-pregna-5,7,17-trien-21-yl ester.

13. A compound according to claim 8 wherein Y is C(O)—OR$^1$— (c).

14. The compound of claim 13, (7E)-(1R,3R)-1,3-dihydroxy-19-nor-9,10-seco-androsta-5,7-diene-17b-carboxylic acid 3-hydroxy-3-methyl-butyl ester.

15. A compound of the formula

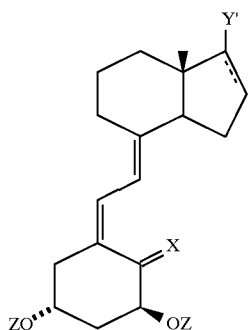

II wherein

Z is a protecting group,

X is =CH$_2$ and Y' is —CH(CH$_3$)—CH$_2$—O—C(O)—R$_2$ (b) or —C(O)—OR$^1$ (c); or X is H,H and Y' is —CH(CH$_3$)—(A)$_n$—C(O)—OR$^1$ (a), —CH(CH$_3$)—CH$_2$—O—C(O)—R$^2$ (b)

or

—C(O)—OR$^1$ (c),

A is —CH=CH— or CH$_2$—CH$_2$—

R$^1$ is lower alkyl, cycloalkyl, cycloalkylmethyl, —CH$_2$R$^3$ or —CH$_2$—CH$_2$R$^3$;

R$^2$ is lower alkyl, cycloalkyl or R$^3$;

R$^3$ is hydroxy-lower alkyl, hydroxy-cycloalkyl or trifluoromethyl-hydroxy-lower-alkyl;

n is 0 or 1;

with the proviso that X is H,H when Y' is —CH(CH$_3$)—CH$_2$—OC(O)—C(OH)(CH$_3$)$_2$ and the dotted bond in the five-membered ring is absent wherein any hydroxy groups contained therein are protected.

16. A pharmaceutical composition comprising an effective amount of a compound of the formula

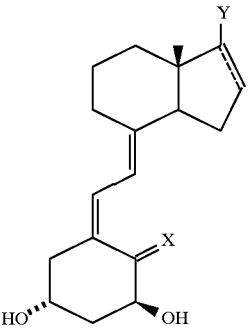

I wherein

X is =CH$_2$ and Y is

—CH(CH$_3$)—CH$_2$—O—C(O)R$_2$ (b)

or

—C(O)—OR$^1$ (c);

or

X is H,H and Y is

—CH(CH$_3$)—(A)$_n$—C(O)—OR$^1$ (a)

—CH(CH$_3$)—CH$_2$—O—C(O)R$^2$ (b)

or

—C(O)—OR$^1$ (c);

A is —CH=CH— or CH$_2$—CH$_2$—

R$^1$ is lower alkyl, cycloalkyl, cycloalkylmethyl, —CH$_2$R$^3$ or —CH$_2$—CH$_2$R$^3$;

R$^2$ is lower alkyl, cycloalkyl or R$^3$;

R$^3$ is hydroxy-lower alkyl, hydroxy-cycloalkyl or trifluoromethyl-hydroxy-lower-alkyl;

n is 0 or 1;

with the proviso that X is H,H when Y is —CH(CH$_3$)—CH$_2$—OC(O)—C(OH)(CH$_3$)$_2$ and the dotted bond in the five-membered ring is absent and a pharmaceutically inert carrier.

17. A process of the preparation of a compound of the formula

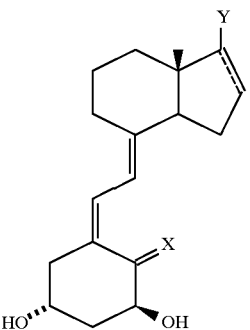

I wherein

X is =CH$_2$ and Y is

—CH(CH$_3$)—CH$_2$—O—C(O)R$^2$ (b)

or

—C(O)—OR¹  (c);

or

X is H,H
and Y is

—CH(CH₃)—A)ₙ—C(O)—OR¹  (a)

—CH(CH₃)—CH₂—O—C(O)R²  (b)

or

—C(O)—OR¹  (c);

A is —CH=CH— or CH₂—CH₂—
R¹ is lower alkyl, cycloalkyl, cycloalkylmethyl, —CH₂R³ or —CH₂—CH₂R³,
R² is lower alkyl, cycloalkyl or R³;
R³ is hydroxy-lower alkyl, hydroxy-cycloalkyl or trifluoromethyl-hydroxy-lower-alkyl;
n is 0 or 1;
with the proviso that X is H,H, when Y is —CH(CH₃)—CH₂—OC(O)—C(OH)(CH₃)₂, and the dotted bond in the five-membered ring is absent, which comprises removing the hydroxy protecting groups from a compound of the formula

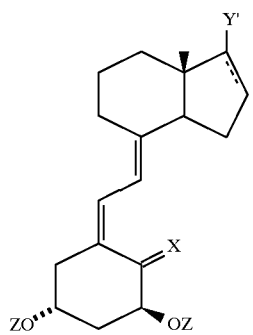

II wherein Z is a protecting group and Y' is Y wherein any hydroxy groups contained therein are protected, with the proviso that the preparation of a compound of the formula I, wherein X is =CH₂, when Y is a moiety —CH(CH₃)—CH₂—OC(O)—C(OH)(CH₃)₂, and the dotted bond in the five-membered ring is absent, is excluded.

18. A method of treating psoriasis comprising administering to a host in need of such treatment an effective amount of a compound of the formula

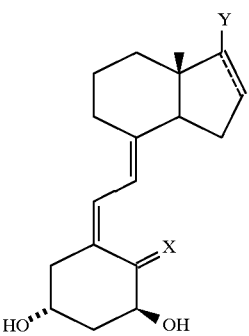

I wherein
X is =CH₂ and Y is

—CH(CH₃)—CH₂—O—C(O)R²  (b)

or

—C(O)—OR¹  (c);

or

X is H,H and Y is

—CH(CH₃)(A)ₙ—C(O)OR¹  (a)

—CH(CH₃)—CH₂—O—C(O)R²  (b)

or

—C(O)—OR¹  (c);

A is —CH=CH— or CH₂—CH₂—
R¹ is lower alkyl, cycloalkyl, cycloalkylmethyl, —CH₂R³ or —CH₂—CH₂R³,
R² is lower alkyl, cycloalkyl or R³,
R³ is hydroxy-lower alkyl, hydroxy-cycloalkyl or trifluoromethyl-hydroxy-lower-alkyl;
n is 0 or 1;
with the proviso that X is H,H when Y is —CH(CH₃)—CH₂—OC(O)—C(OH)(CH₃)₂ and the dotted bond in the five-membered ring is absent.

19. The method of claim 1, wherein the dermatological condition is psoriasis.

20. The method of claim 1 wherein the dermatological condition is acne.

21. The method of claim 1, wherein the dermatological condition is photodamaged skin.

* * * * *